(12) United States Patent
Le Hen Ferrenbach et al.

(10) Patent No.: US 9,730,879 B2
(45) Date of Patent: Aug. 15, 2017

(54) METHOD FOR PRODUCING CARBOHYDRATE PARTIAL ESTERS

(75) Inventors: Catherine Le Hen Ferrenbach, Meaux (FR); Marc Beuche, Vauhallan (FR); Myriam Roussel, Meaux (FR)

(73) Assignee: Cognis IP Management GmbH, Düsseldorf (DE)

( * ) Notice: Subject to any disclaimer, the term of this patent is extended or adjusted under 35 U.S.C. 154(b) by 1420 days.

(21) Appl. No.: 11/719,063

(22) PCT Filed: Oct. 29, 2005

(86) PCT No.: PCT/EP2005/011604
§ 371 (c)(1),
(2), (4) Date: May 10, 2007

(87) PCT Pub. No.: WO2006/050832
PCT Pub. Date: May 18, 2006

(65) Prior Publication Data
US 2008/0108578 A1    May 8, 2008

(30) Foreign Application Priority Data

Nov. 10, 2004  (DE) ........................ 10 2004 054 432

(51) Int. Cl.
| | |
|---|---|
| C07H 1/00 | (2006.01) |
| A61K 8/30 | (2006.01) |
| A61K 8/60 | (2006.01) |
| A61Q 19/00 | (2006.01) |
| C07H 13/06 | (2006.01) |

(52) U.S. Cl.
CPC ................ *A61K 8/60* (2013.01); *A61Q 19/00* (2013.01); *C07H 13/06* (2013.01)

(58) Field of Classification Search
CPC . A61K 8/60; A61Q 19/00; C07H 1/00; C07H 13/06
See application file for complete search history.

(56) References Cited

U.S. PATENT DOCUMENTS

| | | | | |
|---|---|---|---|---|
| 4,897,474 A | * | 1/1990 | Bickert | ......................... 536/119 |
| 5,231,199 A | * | 7/1993 | Willemse | ..................... 554/174 |
| 5,945,519 A | | 8/1999 | Desai et al. | |
| 6,706,877 B1 | * | 3/2004 | Claverie et al. | ............. 536/119 |
| 2005/0037036 A1 | | 2/2005 | Nielsen et al. | |

FOREIGN PATENT DOCUMENTS

| | | |
|---|---|---|
| DE | 4 131 505 | 3/1993 |
| DE | 197 17 968 | 10/1998 |
| DE | 10 2004 054432 | 7/2005 |
| EP | 0 252 250 | 1/1988 |
| EP | 254376 | 1/1988 |
| EP | 322971 | 7/1989 |
| EP | 0 349 221 | 1/1990 |
| EP | 349059 | 1/1990 |
| EP | 548272 | 6/1993 |
| EP | 550526 | 6/1993 |
| EP | 885 898 | 6/1998 |
| EP | 1374853 A1 | 1/2004 |
| FR | 9916213 | 6/2001 |
| WO | WO 92/04360 | 3/1992 |
| WO | WO 92/04361 | 3/1992 |
| WO | 98/22075 A2 | 5/1998 |
| WO | WO 98/22085 | 5/1998 |
| WO | WO 99/37744 | 7/1999 |
| WO | WO 99/38875 | 8/1999 |
| WO | 03/013460 A2 | 2/2003 |

* cited by examiner

*Primary Examiner* — Layla Berry
(74) *Attorney, Agent, or Firm* — Marshall, Gerstein & Borun LLP

(57) ABSTRACT

A process for the production of carbohydrate partial esters by transesterification of glycoses with fatty acid esters in the presence of emulsifiers and a catalyst mixture, to produce products with utility in the production of foods, cosmetic preparations, and in superabsorbancy applications.

18 Claims, No Drawings

US 9,730,879 B2

METHOD FOR PRODUCING CARBOHYDRATE PARTIAL ESTERS

RELATED APPLICATIONS

This application is filed under 35 U.S.C. §371 claiming priority from application PCT/EP2005/011604 filed Oct. 29, 2005, which claims priority from German application DE 10 2004 054 432.8 filed Nov. 10, 2004; the entire contents of each application are incorporated herein by reference.

BACKGROUND OF THE INVENTION

Field of the Invention

This invention relates to the production of carbohydrate partial esters by transesterification of glycoses with fatty acid esters in the presence of emulsifiers and a special catalyst mixture and to the use of the substances obtainable by this process.

Background and Related Art

Carbohydrate esters, which are often also referred to as "sugar esters", are esters of mono- or oligosaccharides and, in a broader sense, of sugar alcohols with organic or inorganic acids. Carbohydrate esters have pronounced surface-active properties, so that they are now regarded as an independent class of compounds (so-called "sugar surfactants"). By virtue of their favorable dermatological and toxicological compatibility, carbohydrate esters are mainly used as emulsifiers for the production of food and cosmetic products. Sucrose polyesters with 6 to 8 fatty acid residues are used in the diets of overweight people as a fat substitute, as they have no value to the organism and, in addition, are said to bind LDL cholesterol in the stomach.

There are various known processes for the production of sugar esters. Normally, glycoses are subjected to a transesterification with fatty acid methyl esters in the presence of alkaline catalysts, and optionally emulsifiers, and in the presence or absence of solvents. The solvent-free variant is preferred, in particular, when the sugar esters are to be used in the food industry. For example, DE 4131505 describes a process for working up sucrose fatty acid esters, which have been produced by the solventless transesterification of sucrose with fatty acid alkyl ester in the presence of a basic transesterification catalyst, the unreacted sucrose being filtered off at a temperature between the melting points of the sucrose used and the sucrose ester produced, and unreacted fatty acid alkyl ester then being distilled off from the reaction mixture. EP 254376 relates to a solventless, complete process for the production of polyol fatty acid esters in which less than half the hydroxyl groups are esterified, a solvent optionally having to be added intermediately in order to form catalytically-active polyol anions. Solventless processes for the production of highly esterified polyol fatty acid esters are also the subject of WO 99/38875, EP 548272, EP 550526, EP 322971 and EP 349059.

A solventless process for the production of sucrose fatty acid esters in the presence of a basic catalyst is the subject of EP 885 898. In this process, sucrose is reacted with fatty acid alkyl esters at 120° to 160° C. under pressures of 25 to 100 mbar, after which the temperature is reduced to 90° to 130° C., and the resulting reaction product is filtered without addition of a solvent. This process provides dark brown, viscous crude products, which are bleached in a following step. A process for the production of polyol polyesters with improved color quality is the subject of EP 349221. In this process, $C_{1-3}$-alkyl fatty acid esters, having a carbonyl content of less than 200 ppm, are reacted with a polyol in the presence of a catalyst and, at the same time, the alcohol formed is removed from the equilibrium.

DE 19717968 describes a process for the production of carbohydrate partial esters in which the alkali-catalyzed transesterification is carried out in the presence of emulsifiers and a catalytically-active system of alkali metal carbonates, with fatty acid lower alkyl esters being formed in a first step and then reacted with glycoses and carbohydrate partial esters as emulsifiers. This process also provides relatively strongly-colored crude products, which also have a high ash content (DGF Methoden "Asche C III, 1097). FR 9916213 describes mixtures based on 10 to 90%, by weight sugar esters and 90 to 10%, by weight hydrocarbons, which are used in cosmetic formulations. However, pelleted compositions of these mixtures secrete oil after brief storage.

The solventless processes normally provide a complex reaction mixture which, to a large extent, contains unreacted starting products that are difficult to remove. These products are often very dark in color. Lighter-colored products are obtained by processes, such as that described in EP 349221. However, these processes require prepurified fatty acid alkyl esters, requiring an additional reaction step.

The problem addressed by the present invention was to provide an alternative economical, solventless process with high yields and short reaction times, which would give crude products with improved color and a reduced ash content, and which would not require prepurification of the starting materials.

It has surprisingly been found that a significant process improvement may be achieved if a mixture of alkali metal carbonate and alkali metal hypophosphite is used as the catalyst mixture.

SUMMARY OF THE INVENTION

The present invention relates to a solventless process for the production of carbohydrate partial esters, having an average degree of esterification of 1 to 4, by alkali-catalyzed esterification in the presence of a catalyst mixture of alkali metal carbonate(s) and alkali metal hypophosphite(s), characterized in that (a) at least one alkali metal carbonate and at least one fatty acid alkyl ester corresponding to formula (I):

$$R^1CO\text{—}OR^2 \qquad (I),$$

in which $R^1CO$ is a linear or branched, saturated or unsaturated acyl group containing 6 to 30 carbon atoms, and $R^2$ is a linear or branched alkyl group containing 1 to 5 carbon atoms, are mixed to form a catalytically-active system; and (b) glycoses containing 5 to 12 carbon atoms, carbohydrate partial esters as emulsifiers and one or more alkali metal hypophosphites are added with continuous stirring to the mixture resulting from step (a), so that a dispersion is formed, and water is removed from the resulting mixture with continuous stirring at temperatures of up to 100° C. and under a pressure of up to 50 mbar; and (c) the esterification reaction is continued under a pressure of up to 50 mbar, and at temperatures of up to 125° C., with continuous stirring until the content of fatty acid alkyl esters of formula (I) has fallen to at least 8% by weight, based on the composition as a whole, steps (a) to (c) optionally being carried out in an inert gas atmosphere.

In the process according to the invention, the catalyst combination of alkali metal carbonate and alkali metal hypophosphite gives color-improved products, with a lower ash content, in high yields, and with comparatively shorter reaction times. In addition, the formation of secondary products, such as soap, is reduced. Nitrogen is preferably used as the inert gas. The use of inert gases provides for even lighter-colored products.

DETAILED DESCRIPTION OF THE INVENTION

In the first step, (a), of the process, a coating of fatty acid lower alkyl ester is formed on the alkali metal carbonate, so that the acyl group is activated. In the second step, the activated catalyst is contacted with a mixture of a glycose, alkali metal hypophosphite and a carbohydrate partial ester, the carbohydrate partial ester acting as an emulsifier. According to the invention, the alkali metal hypophosphite may even be added in step (a). This alternative procedure is regarded as equivalent in the context of the invention.

During the reaction, acyl groups are transferred to the emulsifier which itself acts as an acylating agent in the further course of the reaction and transfers acyl groups to the glycose, which is thus converted into a carbohydrate partial ester. The reaction takes place in the absence of solvents, which is of considerable advantage both from the economy perspective and with regard to the use of the end products in the food or cosmetic sector. Another unexpected advantage of the process is that, despite reduction of the alkali metal catalyst, an effective reaction is obtained in comparably short reaction times with improved color quality.

Catalysts

According to the invention, a combination of alkali metal carbonate(s) and alkali metal hypophosphite(s) is used as the catalyst. Sodium and/or potassium carbonate and sodium and/or potassium hypophosphite are preferably used. According to the invention, it is of advantage to use 0.06 to 0.6 mol of alkali metal carbonate and 0.01 to 0.1 mol of alkali metal hypophosphite per mol of glycose. A particularly advantageous embodiment of the invention is characterized by the use of 0.07 to 0.3 mol of potassium carbonate and 0.01 to 0.05 of mol sodium hypophosphite per mol of glycose, preferably 0.08 to 0.2 mol of potassium carbonate and 0.01 to 0.03 mol of sodium hypophosphite per mol of glycose and more particularly 0.1 to 0.15 mol of potassium carbonate and 0.012 to 0.02 mol sodium hypophosphite per mol of glycose.

Fatty Acid Lower Alkyl Esters

Typical examples of suitable acylating agents are the esters of caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid, and technical mixtures thereof, with methanol, ethanol, propanol, isopropyl alcohol, n-butanol, i-butanol, tert. butanol, n-pentanol and isopentanol. Esters of formula (I), in which $R^2$ is a methyl and/or ethyl group, are preferably used. Another preferred variant is characterized by the use of fatty acid alkyl esters (a2) with linear saturated acyl groups containing 12 to 30 carbon atoms and preferably 16 to 24 carbon atoms. $C_{16}$-$C_{24}$ fatty acid methyl esters, and especially $C_{16}$-$C_{20}$ fatty acid methyl esters, are particularly preferred, linear and unbranched esters being particularly preferred for the purposes of the invention. According to the invention, it is of advantage to use $C_{16}$ fatty acid methyl esters or $C_{18}$ fatty acid methyl esters or mixtures of $C_{16}$ and $C_{18}$ fatty acid methyl esters, for example, with a $C_{16}/C_{18}$ ratio of 50:50, or 30:70, or 70:30.

The molar ratio of fatty acid alkyl ester (a2) to glycose (b1) is preferably at least 0.5:1, more particularly 0.5-2.5:1 and, in a particularly preferred embodiment, 0.6-2.0:1. With lower molar ratios, the reaction products are increasingly colored and viscous, which is presumably attributable to caramelization of the sugar. According to the invention, a molar ratio of 1.3-1.6:1 and more particularly 1.4-1.55:1, is particularly preferred for reducing caramelization of the sugar and obtaining lighter-colored crude products.

Production of the Catalyst System

To produce the catalyst system, i.e., to activate the fatty acid alkyl ester as the acylating agent, the fatty acid alkyl ester and the alkali metal carbonate are mixed with vigorous stirring. According to the invention, it has proven to be of advantage in this regard to produce the catalytically-active system at temperatures in the range of from 50 to 100° C., and preferably at temperatures in the range of from 60 to 90° C. More particularly, the temperature in the case of solid fatty acid alkyl ester should be above the melting point of the ester in order to achieve uniform dispersion. The ester presumably undergoes chemisorption onto the surface of the carbonate. To produce a fine-particle dispersion, the system is normally vigorously stirred continuously for ca. 15 to 60 minutes, and preferably for ca. 15 to 30 minutes, at a temperature in the above-mentioned range. On an industrial scale, the Sigmarührer® SIR (manufactured by Steizer), for example, with a total of 5 impellers on the stirrer shaft, is suitable for this purpose.

Glycoses

The glycoses include the polyhydroxyaldehydes (aldoses) and polyhydroxyketones (ketoses), also referred to as carbohydrates, and relatively high molecular weight compounds, which may be converted into such substances by hydrolysis. Both the monomeric polyhydroxyaldehydes or polyhydroxyketones (monosaccharides) and dimers-to-decamers thereof (disaccharides, trisaccharides, oligosaccharides), may be used as glycoses in accordance with the invention. Suitable monosaccharides (also termed "simple sugars") are, for example, bioses, trioses, tetraoses, pentoses, hexoses, heptoses, etc. Typical examples of aldopentoses are D-ribose, D-xylose and L-arabinose. The most important aldohexoses include D-glucose, D-mannose and D-galactose; among the ketohexoses, D-fructose and sorbose may be mentioned. The 6-deoxysugars, L-fucose and L-rhamnose, are also widely used hexoses and may also be used as starting materials. The most simple oligosaccharides suitable as starting materials are the disaccharides. Sucrose (cane sugar, beet sugar), lactose (milk sugar) and/or maltose (malt sugar) is/are preferably used. Mono- and/or disaccharides are preferably used in the process, sucrose or glucose being particularly preferred.

Emulsifiers

According to the invention, it has proven to be of particular advantage to use as emulsifiers partial esters of carbohydrates, of which the carbohydrate unit is identical with those of the target products. A particularly advantageous embodiment of the invention is characterized by the use of carbohydrate partial esters, in which both the carbohydrate unit and the ester residue correspond with those of the target products, i.e., which may only differ in the degree of esterification. A particularly preferred embodiment is characterized by the use of sucrose partial esters, with an average degree of esterification of 2 to 6, and more particularly 3 to 4. Suitable sugar esters are, for example, Sisterna® SP 01, Sisterna® SP 30 and Sisterna® SP 50. According to the invention, preferred emulsifiers are sugar esters with a low percentage, by weight, of monoester of preferably less than 30%, by weight, and, more particularly, less than 1%, by weight, monoester. A particularly preferred embodiment of the invention is characterized by the use of partial esters of sucrose with $C_{16}$ and/or $C_{18}$ fatty acids, with a correspondingly low monoester content, because they reduce the reaction time and contribute to a fast reaction. The carbohydrate partial esters may be used in powder form, in liquid form or even in pelleted form. For example, it has proven to be of advantage to use pellets of sucrose partial esters with the fatty acid methyl esters, which are also used as reactants.

Suitable additional co-emulsifiers are, for example, non-ionic surfactants from at least one of the following groups:
(1) products of the addition of 2 to 30 mol of ethylene oxide and/or 0 to 5 mol of propylene oxide onto linear fatty alcohols containing 8 to 22 carbon atoms, onto fatty acids containing 12 to 22 carbon atoms and onto alkyl phenols containing 8 to 15 carbon atoms in the alkyl group;
(2) $C_{12\text{-}18}$ fatty acid mono- and diesters of addition products of 1 to 30 mol of ethylene oxide onto glycerol;
(3) glycerol mono- and diesters and sorbitan mono- and diesters of saturated and unsaturated fatty acids containing 6 to 22 carbon atoms, and ethylene oxide addition products thereof;
(4) alkyl mono- and oligoglycosides containing 8 to 22 carbon atoms in the alkyl group, and ethoxylated analogs thereof;
(5) products of the addition of 15 to 60 mol of ethylene oxide onto castor oil and/or hydrogenated castor oil;
(6) polyol and, in particular, polyglycerol esters, such as, for example, polyglycerol polyricinoleate or polyglycerol-12-hydroxystearate. Mixtures of compounds from several of these classes are also suitable;
(7) products of the addition of 2 to 15 mol ethylene oxide onto castor oil and/or hydrogenated castor oil;
(8) partial esters based on linear, branched, unsaturated or saturated $C_{6\text{-}22}$ fatty acids, ricinoleic acid and 12-hydroxystearic acid, and glycerol, polyglycerol, pentaerythritol, dipentaerythritol, sugar alcohols (for example, sorbitol), alkyl glucosides (for example, methyl glucoside, butyl glucoside, or lauryl glucoside) and polyglucosides (for example, cellulose);
(9) trialkyl phosphates and mono-, di- and/or tri-PEG-alkyl phosphates;
(10) wool wax alcohols;
(11) polysiloxane/polyalkyl polyether copolymers and corresponding derivatives;
(12) mixed esters of pentaerythritol, fatty acids, citric acid and fatty alcohol and/or mixed esters of fatty acids containing 6 to 22 carbon atoms, methyl glucoside and polyols, preferably glycerol, and
(13) polyalkylene glycols.

The molar ratio of carbohydrate partial ester to glycose is preferably 0.03 to 0.25:1, preferably 0.04 to 0.2:1 and more particularly 0.09 to 0.12:1.

A preferred embodiment of the process according to the invention is characterized in that the molar ratio of alkali metal carbonates:fatty acid alkyl esters:glycoses:carbohydrate partial esters:alkali metal hypophosphites varies in the range of (0.06-0.6):(0.6-2.0):1:(0.04-0.2):(0.01-0.1).

Carrying Out the Reaction

The reaction is carried out by preparing an emulsion or dispersion with vigorous stirring, the emulsion/dispersion containing the catalyst system, the glycose and the carbohydrate ester and, optionally, other emulsifiers. In the case of medium- to high-viscosity mixtures, the mechanical stirring on an industrial scale is carried out using a stirring system of impellers in combination with flow disrupters at rotational speeds of 50 to 400 r.p.m. and preferably 100 to 300 r.p.m.

The pressure in step (b) and in step (c) is preferably, at most, 25 mbar, more preferably, at most, 15 mbar and, most preferably, at most, 10 mbar. These pressure conditions ensure that water is efficiently removed from the reaction equilibrium. More particularly, the "predrying" in step (b) is intended to remove the residual water emanating from the raw materials.

Step (b) is preferably carried out at temperatures of 70° to 85° C., and more particularly, at temperatures of 75° to 80° C., and under a pressure of 1 to 25 mbar, and preferably, under a pressure of 1 to 15 mbar. The actual esterification reaction, step (c), is preferably carried out at temperatures of 100° to 125° C., more preferably at temperatures of 110° to 120° C., and, most preferably, at temperatures of 115° to 120° C., and under a pressure of 1 to 25 mbar, preferably under a pressure of 1 to 15 mbar, and, more particularly, under a pressure of 1 to 10 mbar. The esterification reaction (c) is continued until the content of fatty acid alkyl esters of formula (I) has fallen to at least 8%, by weight, and preferably to at least 5%, by weight, based on the composition as a whole.

The reaction times are normally between 5 and 15 h and may be considerably reduced by efficient stirring.

The products thus produced typically have the following distribution: 5 to 20%, by weight, monoesters, 15 to 30%, by weight, diesters, 20 to 40%, by weight, triesters, and 30 to 40%, by weight, tetraesters, plus a small percentage of higher homologs. The percentage content of unreacted glycoses in the crude product is typically, at most, 15% by weight, and preferably, at most, 10%, by weight.

In another preferred embodiment, a gentle stream of inert gas (nitrogen) is passed through the reaction mixture without departing from the pressure conditions mentioned above, which leads to lighter-colored products.

Working Up the Crude Mixture

In a preferred variant of the process according to the invention, the hot reaction product is dissolved in an emollient suitable for cosmetic applications and/or for foods and, after removal of the unreacted glycoses, is bleached with hydrogen peroxide, preferably in a nitrogen atmosphere, optionally treated with an acid to adjust a pH of 6 to 8, and then optionally filtered through a filtration aid. In the context of the invention, emollients are understood to be oil components which are liquid at 60° C., preferably even at 40° C. and, more particularly, even at 20° C., and normal pressure. The emollients have to be able to dissolve the carbohydrate partial esters produced by the process according to the invention, either at room temperature, or optionally with heating. Other suitable emollients are oil components, which are solid, paste-like or wax-like at room temperature, but which in the molten state have a high solvent power for the carbohydrate partial esters. Oil components suitable for the purposes of the invention are, for example, hydrocarbons, ester oils, polyols, dialkylethers, dialkyl carbonates, such as, for example, Cetiol® S, Sylko® 365 NF, Panalane® L 14 E, Cetiol® NPC, Cetiol® SN, Cetiol® PGL, Edenor® V, Cetiol® OE, and Cetiol® CC. According to the invention, particularly suitable oil components are hydrocarbons and, among these, a polyisobutene liquid at normal pressure, more particularly the hydrogenated polyisobutene, which is marketed under the name of Panalane® L14E (manufactured by Amoco; INCI name: Hydrogenated Polyisobutene). Besides its low viscosity, this hydrogenated polyisobutene has very good dissolving properties for the sucrose esters produced in accordance with the invention, and has sensory advantages in regard to the final cosmetic formulations. Liquid, paste-like or wax-like ester oils of $C_{6-22}$ fatty acids and $C_{1-3}$ alcohols such as, for example, Edenor® ME 16V, are also suitable as solvents for carbohydrate partial esters produced in accordance with the invention.

The unreacted glycoses may be removed, for example, by decantation, centrifuging or filtration. In a preferred embodiment of the invention, they are removed by filtration, preferably using heatable filters, and preferably at 60 to 80° C.

Suitable filters are, for example, filters based on cellulose and silica, such as Fibra Fix® AF6 from Filtrox AG, with a throughput of ca. 2800 to 3600 l/m² per minute (based on water at 100 kPa), which is suitable for crude filtration. Suitable filtration aids are, for example, Hyflo Super Cel® (Lehmann & Voss), Becolite® 5000 (Begerow Chemie), Arbocel® BC 200 and B600, Filtracel® AFC 1400 (J. Rettenmaier & Söhne GmbH & Co.), TriSyl® or TriSyl® 2 (Grave Davison), bleaching earths (for example, Tonsil® from Süd-Chemie) and silicas, for example, diatomaceous earths, such as Seitz Ultra® (Pall Corporation).

Cloudy or clear, viscous, more or less colored products are obtained depending on the filtration aid. The products are clearly lighter in color than is the case where alkali metal carbonates alone are used. According to the invention, silicas have proven to be particularly effective in terms of color quality and filtration throughput. The product marketed under the name of Seitz Ultra® is particularly suitable for the purposes of the invention. In the filtration step, the filtration aid is added, the mixture is homogenized with continuous stirring, and then filtered. Products with a residual sugar content of less than 10%, by weight, and more particularly below 5%, by weight, based on the overall composition of the product mixture, are normally obtained after the first filtration. This first filtration step is followed by a bleaching step with hydrogen peroxide, which is preferably carried out in a nitrogen atmosphere. The reaction product is then dried again, in vacuo, to remove residues of water. The pH of the product mixture should be between 6 and 8, and is optionally adjusted by the addition of acid, such as with usual mineral acids or fruit acids. According to the invention, the addition of citric acid or lactic acid is particularly suitable, with lactic acid being more particularly suitable, as the products thus neutralized lead to more stable final cosmetic formulations.

The filtration step is optionally repeated several times to minimize the residual sugar content, which minimization is advantageous for obtaining products of high color quality. The higher the residual sugar content, the darker the products, and the more they tend to turn even darker in color with time. These filtrations may be carried out using filters with a permeability of ca. 240 to 300 l/m² per minute (based on water at 100 kPa). For example, Fibra Fix® AF 41H from Filtrox AG, a filter based on cellulose and inorganic additives is suitable for the purposes of the invention.

In order to minimize the content of free fatty acid and soap in the end product, the aftertreatment steps for working up the crude mixture should be carried out in the shortest possible time.

In a preferred variant of the process according to the invention, a $C_{16-40}$ fatty alcohol, preferably a $C_{18-30}$ fatty alcohol, and more particularly, a $C_{20-24}$ fatty alcohol, or a mixture of these fatty alcohols, is added to the solution of the carbohydrate partial ester and, optionally, after bleaching with hydrogen peroxide, the product is pelleted, extruded, granulated, crystallized, spray-dried or tabletted. The fatty alcohol is normally added to the hot solution at ca. 70° to 85° C. In a preferred embodiment of the invention, 1 to 10%, by weight, and preferably 1 to 5%, by weight, of a $C_{16-40}$ fatty alcohol, or a mixture of such fatty alcohols, based on the resulting overall composition, is added. Only the addition of the fatty alcohols enables shaped bodies to be obtained which secrete no more oil (for example, hydrocarbons). Shaped bodies without fatty alcohols secrete oil with time, i.e., they "sweat" and are therefore less stable in storage. $C_{20-24}$ fatty alcohols have proven to be advantageous for the purposes of the invention.

According to the invention, it is particularly suitable to add the $C_{22}$ fatty alcohol, behenyl alcohol, which is marketed under the name of Lanette® 22 by Cognis Deutschland GmbH & Co. KG, more particularly in a quantity of 1 to 5%, by weight, and preferably in a quantity of 1 to 3% by weight, based on the final formulation.

The present invention also relates to shaped bodies containing: (a) carbohydrate partial esters obtainable by the process of the invention; (b) an emollient suitable for cosmetic applications and/or foods; and (c) 1 to 10%, by weight, of a $C_{16}$-$C_{40}$ fatty alcohol, or a mixture of such fatty alcohols, the content of other auxiliaries and additives being, at most, 20%, by weight. A preferred embodiment of the shaped body contains: (a) 10 to 80%, by weight, of a carbohydrate partial ester or a mixture of carbohydrate partial esters, obtainable by the process of the invention; (b) 10 to 20%, by weight, of an emollient suitable for cosmetic applications and/or foods; and (c) 1 to 10%, by weight, of a $C_{16}$-$C_{40}$ fatty alcohol or a mixture of such fatty alcohols, the content of other auxiliaries and additives being, at most, 10%, by weight. The content of other auxiliaries and additives is preferably less than 10%, by weight, and more particularly less than 5%, by weight, based on the composition as a whole. In a most preferred embodiment, the percentage content of other auxiliaries and additives is limited solely to secondary products, which are present in the product mixture from the reaction. The definition of emollient is the same as for the process (vide supra). According to the invention, suitable emollients are the substances already mentioned in the foregoing, for example, hydrocarbons, ester oils, polyols, dialkyl ethers, dialkyl carbonates, such as Cetiol® S, Sylko® 365 NF, Panalane® L 14 E, Cetiol® NPC, Cetiol® SN, Cetiol® PGL, Edenor® V, Cetiol® OE, Cetiol® CC. According to the invention, particularly suitable emollients are hydrocarbons and, among these, a polyisobutene liquid at normal pressure, more particularly, the hydrogenated polyisobutene, which is marketed under the name of Panalane® L14E (cited above). Liquid, paste-like or wax-like ester oils of $C_{6-22}$ fatty acids and $C_{1-3}$ alcohols, such as, for example, Edenor® ME 16V are also particularly suitable as solvents for carbohydrate partial esters produced in accordance with the invention. According to the invention, preferred fatty alcohols are the same as those mentioned for the process (vide supra). The shaped bodies according to the invention are preferably obtained by pelleting, extrusion, granulation, spray drying, crystallization, tabletting or by coating. The relevant processes are well-known to the expert and are described in the literature.

Commercial Applications

The carbohydrate esters obtainable by the process according to the invention have excellent surface-active properties, and may be used, for example, as emulsifiers for the production of foods (bread, confectionery, ice creams, etc.) and cosmetic preparations in which they may be present in quantities of 0.1 to 20%, by weight, preferably 1 to 10%, by weight, and more particularly 1 to 5%, by weight. The carbohydrate esters according to the invention may also be used as emulsifiers for the production of polyacrylic and polymethacrylic acid compounds which may, in turn, be used as "superadsorbers", for example, for diapers. Since the emulsifiers remain in the end product, not only are their excellent performance properties, but also their particular dermatological compatibility, relevant in this regard.

The present invention also relates to the use of the carbohydrate partial esters produced by the process according to the invention as emulsifiers in foods and cosmetic or pharmaceutical preparations.

The present invention also relates to cosmetic preparations containing 0.1 to 20%, by weight, and preferably 0.5 to 7%, by weight of the shaped bodies according to the invention, and to their use for the production of cosmetic preparations. They contribute towards the creation of lamellar structures which provide the final formulations with particular stability.

Accordingly, the present invention also relates to the use of the shaped bodies according to the invention for creating lamellar structures in oil-in-water emulsions.

Depending on their intended application, the cosmetic formulations contain a number of other auxiliaries and additives, such as, for example, thickeners, superfatting agents, stabilizers, polymers, lecithins, phospholipids, biogenic agents, UV protection factors, antioxidants, deodorants, film formers, swelling agents, insect repellents, hydrotropes, solubilizers, preservatives, perfume oils, dyes, and the like. The quantities in which the particular additives are used are governed by the intended application for the final product.

The following Examples are intended to exemplify the present invention, and should not be interpreted as limiting to it.

EXAMPLES

Example 1 (Laboratory Scale)

The synthesis was carried out in a gentle stream of nitrogen introduced into the reaction mixture.

636.7 g (2.2 mol) of hydrogenated palm fatty acid methyl ester (Edenor® ME AS 16 V) were introduced into a 2 kg double-jacketed glass reactor, heated to 65° C., and equipped with a high-speed stirrer, reflux condenser and dropping funnel. 26.7 g (0.19 mol) of potassium carbonate, corresponding to 4%, by weight, based on the methyl ester, were then added at a stirrer speed of 1300 r.p.m., and the mixture was stirred for 10 minutes. 134 g (0.16 mol) of sucrose distearate (Sisterna® SP 30C) were added, in portions, to the dispersion thus obtained, and, after stirring for 10 minutes at 1500 r.p.m., 503 g (1.47 mol) of sucrose (powdered sugar from Beguin Say) were added, followed by stirring for 20 minutes at 2000 r.p.m 2 g (0.023 mol) of sodium hypophosphite were then added, the stirrer speed being kept at 2000 r.p.m. The resulting emulsion/dispersion was heated to 85° C., under a pressure of 1 to 5 mbar, followed by stirring for another 30 minutes. The temperature was then slowly increased to 125° C. and the reaction mixture was stirred for another 11 h at a stirrer speed of 2000 r.p.m. A sucrose ester containing 14%, by weight, monoester, 22%, by weight, diester, 30%, by weight triester, and 34%, by weight, tetraester and higher homologs, based on the total quantity of carbohydrate ester, was obtained. The content of unreacted ester in the reaction mixture was ca. 5%, by weight, and the content of free sucrose 4%, by weight.

Working Up:

After the reaction mixture had been cooled to ca. 110° C., 244 g of Panalane L 14 E (Amoco) were added and the mixture was homogenized by stirring for ca. 15 minutes. The hot solution was filtered off through a filter, using Seitz Ultra® as a filtration aid, and was bleached for 1 hour under nitrogen with 15 ml (0.29 mol) of a 35% (% by weight) hydrogen peroxide solution. The pH was adjusted by addition of 7.2 ml of an 80% lactic acid solution (% by weight), and the solution was subjected to another filtration with Seitz Ultra®. 2% by weight (based on the composition as a whole) of behenyl alcohol was added at 80° C. and, after homogenization by stirring, the product was pelleted.

Example 2 (Industrial Scale)

The reaction was carried out as in Example 1, after scaling up to an industrial scale. 887 kg palm fatty acid methyl ester, 37 kg catalyst mixture (potassium carbonate and sodium hypophosphite), 187 kg sucrose distearate and 700 kg sucrose were reacted with one another. A sucrose ester containing 12.3%, by weight, monoester, 25.1%, by weight, diester, 33.1%, by weight, triester, 31.5%, by weight, tetraester and higher homologs, based on the total quantity of carbohydrate ester, was obtained. The content of unreacted ester in the reaction mixture was ca. 6%, by weight. Working up was carried out as in Example 1.

Working Up

The product obtained in Example 2 was worked up with a hydrogenated palm fatty acid methyl ester (Edenor® ME AS 16V) instead of Panalane L 14 E.

After the reaction mixture had been cooled to ca. 100° C., 320 kg of palm fatty acid methyl ester (Edenor® ME AS 16 V; Cognis) were added and the mixture was homogenized by stirring for ca. 45 minutes. The hot solution was filtered off through a filter, using Seitz Ultra® as a filtration aid, and was bleached for 45 minutes, under nitrogen, at 85° C. with 10 kg of a 35% (% by weight) hydrogen peroxide solution. The pH was adjusted by addition of 9 kg of an 80% lactic acid solution (% by weight) and the solution was subjected to another filtration with Seitz Ultra®.

TABLE 1

Assessing the influence of the quantity of catalyst, potassium carbonate (comparison), on the conversion of the fatty acid methyl ester The reaction was carried out as in Example 1. A $C_{16}/C_{18}$ fatty acid methyl ester with a ratio of $C_{16}:C_{18}$ fatty acid of 50:50 was used as the fatty acid methyl ester (ME). Sisterna ® SP 30 C was used as the carbohydrate partial ester (SE). The % by weight catalyst ($K_2CO_3$) relates to the content in the composition as a whole. The expression of the conversion in % relates to %, by weight, of the fatty acid methyl ester in the reaction mixture as a whole.

|  | $K_2CO_3$ 5% bw C1 Conversion % ME | $K_2CO_3$ 2.5% bw C2 Conversion % ME | $K_2CO_3$ 1.5% bw C3 Conversion % ME |
|---|---|---|---|
| 3 h | 31.2 | 30.9 | 41.1 |
| 4 h | 27.5 | 27.3 |  |
| 5 h | 22.0 | 28.9 | 31.4 |
| 6 h | 19.1 |  |  |
| 7 h | 15.7 | 24.8 | 23.8 |
| 8 h | 10.7 |  |  |
| 9 h |  | 10.2 | 19.5 |
| 10 h |  | 7.1 |  |
| 11 h |  |  | 13.0 |

TABLE 1-continued

Assessing the influence of the quantity of catalyst, potassium carbonate (comparison), on the conversion of the fatty acid methyl ester The reaction was carried out as in Example 1. A $C_{16}/C_{18}$ fatty acid methyl ester with a ratio of $C_{16}:C_{18}$ fatty acid of 50:50 was used as the fatty acid methyl ester (ME). Sisterna ® SP 30 C was used as the carbohydrate partial ester (SE). The % by weight catalyst ($K_2CO_3$) relates to the content in the composition as a whole. The expression of the conversion in % relates to %, by weight, of the fatty acid methyl ester in the reaction mixture as a whole.

|  | $K_2CO_3$ 5% bw C1 Conversion % ME | $K_2CO_3$ 2.5% bw C2 Conversion % ME | $K_2CO_3$ 1.5% bw C3 Conversion % ME |
|---|---|---|---|
| ME | 475 g | 287.5 g | 640.2 g |
| SE | 100 g | 102.6 g | 123.8 g |
| $K_2CO_3$ | 50 g | 25 g | 19.5 g |
| Sucrose | 375 g | 384.9 g | 505.4 g |

TABLE 2

Comparison between the catalyst mixture (B1) according to the invention and alkali metal carbonates (C4 and C5) The reaction was carried out as in Example 1. A $C_{16}/C_{18}$ fatty acid methyl ester with a ratio of $C_{16}:C_{18}$ fatty acid of 50:50 was used as the fatty acid methyl ester (ME). Sisterna ® SP 30 C was used as the carbohydrate partial ester (SE). The % by weight catalyst ($K_2CO_3$ as C4; $K_2CO_3$ and $NaH_2PO_2$ as B1 and $Na_2CO_3$ as C5) relates to the content in the composition as a whole. The expression of the conversion in % relates to % by weight of the fatty acid methyl ester in the reaction mixture as a whole.

|  | $K_2CO_3$ 2.5% bw C4 Conversion % ME | 2.5% bw $K_2CO_3$ 0.2% bw $NaH_2PO_2$ B1 Conversion % ME | 1.9% bw $Na_2CO_3$ C5 Conversion % ME |
|---|---|---|---|
| 3 h | 30.9 | 28.4 | 42.2 |
| 4 h | 27.3 |  |  |
| 5 h | 28.9 | 19.7 | 38.1 |
| 6 h |  |  |  |
| 7 h | 24.8 | 13.3 | No further change |
| 8 h |  |  | No further change |
| 9 h | 10.2 |  | No further change |
| 10 h | 7.1 | 3.9 | No further change |
| ME | 487.5 g | 634.3 g | 637.5 g |
| SE | 102.6 g | 133.4 g | 134.2 g |
| $K_2CO_3$ | 2.5 g | 32.5 g | — |
| Sucrose | 384.5 g | 500.4 g | 503.4 g |
| $Na_2CO_3$ | — | — | 25 g |

TABLE 3

Catalyst compositions according to the invention and percentage conversion of the $C_{16/18}$ fatty acid methyl ester The reaction was carried out as in Example 1. A $C_{16}/C_{18}$ fatty acid methyl ester with a ratio of $C_{16}:C_{18}$ fatty acid of 50:50 was used as the fatty acid methyl ester (ME). Sisterna ® SP 30 C was used as the carbohydrate partial ester (SE). The %, by weight, of the catalyst mixture according to the invention relates to the content in the composition as a whole. The expression of the conversion in % relates to %, by weight, of the fatty acid methyl ester in the reaction mixture as a whole.

|  | 2.5% bw $K_2CO_3$ 0.2% bw $NaH_2PO_2$ B2 Conversion % ME | 1.9 % bw $K_2CO_3$ 0.1% bw $NaH_2PO_2$ B3 Conversion % ME | 1.5% bw $K_2CO_3$ 0.5% bw $NaH_2PO_2$ B4 Conversion % ME |
|---|---|---|---|
| 3 h | 28.4 |  | 24.5 |
| 4 h |  |  |  |
| 5 h | 19.7 |  | 21.5 |
| 6 h |  |  |  |
| 7 h | 13.3 | 9.2 | 15.6 |
| 8 h |  |  |  |

TABLE 3-continued

Catalyst compositions according to the invention and percentage conversion of the $C_{16/18}$ fatty acid methyl ester The reaction was carried out as in Example 1. A $C_{16}/C_{18}$ fatty acid methyl ester with a ratio of $C_{16}:C_{18}$ fatty acid of 50:50 was used as the fatty acid methyl ester (ME). Sisterna ® SP 30 C was used as the carbohydrate partial ester (SE). The %, by weight, of the catalyst mixture according to the invention relates to the content in the composition as a whole. The expression of the conversion in % relates to %, by weight, of the fatty acid methyl ester in the reaction mixture as a whole.

|  | 2.5% bw $K_2CO_3$ 0.2% bw $NaH_2PO_2$ B2 Conversion % ME | 1.9 % bw $K_2CO_3$ 0.1% bw $NaH_2PO_2$ B3 Conversion % ME | 1.5% bw $K_2CO_3$ 0.5% bw $NaH_2PO_2$ B4 Conversion % ME |
|---|---|---|---|
| 9 h |  | 4.8 |  |
| 10 h | 3.9 |  | 6.3 |
| 11 h |  | 3.6 |  |
| ME | 634.3 g | 636.7 g | 637 g |
| SE | 133.4 g | 134 g | 134.2 g |
| $K_2CO_3$ | 32.5 g | 24.7 g | 19.2 g |
| $NaH_2PO_2$ | 2.6 g | 2 g | 6.5 g |
| Sucrose | 500.4 g | 502.6 g | 502.8 g |

What is claimed is:

1. A solventless process for the production of carbohydrate partial esters, comprising the steps of:
    (a) mixing, in the absence of solvent, $C_{16}/C_{18}$ fatty acid methyl esters and potassium carbonate to form a catalytically-active system; and
    (b) adding, with continuous stirring, one or more glycoses containing 5 to 12 carbon atoms, and one or more emulsifiers comprising carbohydrate partial esters, to said catalytically-active system from step (a), wherein an esterification reaction dispersion is formed;
    wherein the improvement comprises increasing the esterification reaction rate by the steps of:
    (c) adding sodium hypophosphite prior to mixing in step (a) or prior to stirring in step (b);
    (d) removing water from the resulting mixture with continuous stirring at a temperature of up to 100° C., and under a pressure of up to 50 mbar; and
    (e) continuing the esterification reaction under a pressure of up to 50 mbar and at a temperature of up to 125° C., with continuous stirring, until the content of the $C_{16}/C_{18}$ fatty acid methyl esters has fallen to at least 8%, by weight, based on the composition as a whole;
    wherein the potassium carbonate is mixed in an amount of 0.06 mol to 0.16 mol per mol of glycoses;
    wherein the sodium hypophosphite is added in an amount of 0.01 mol to 0.1 mol per mol of glycoses; and
    wherein the so-produced carbohydrate partial esters have an average degree of esterification of 1 to 4.

2. A solventless process for increasing a reaction rate of an esterification reaction for production of carbohydrate partial esters in the presence of a reduced amount of a catalyst mixture of one or more alkali metal carbonates, the process comprising the steps of:
    (a) mixing, in the absence of solvent, $C_{16}/C_{18}$ fatty acid methyl esters and potassium carbonate to form a catalytically-active system;
    (b) adding, with continuous stirring, one or more glycoses containing 5 to 12 carbon atoms, and one or more emulsifiers comprising carbohydrate partial esters, to said catalytically-active system from step (a), wherein a dispersion is formed, and removing water from the resulting mixture with continuous stirring at a temperature of up to 100° C., and under a pressure of up to 50 mbar;

adding sodium hypophosphite prior to mixing in step (a) or prior to stirring in step (b); and (c) continuing the esterification reaction under a pressure of up to 50 mbar and at a temperature of up to 125° C., with continuous stirring, until the content of the $C_{16}/C_{18}$ fatty acid methyl esters has fallen to at least 8% by weight, based on the composition as a whole;

wherein the potassium carbonate is mixed in an amount of 0.06 mol to 0.16 mol per mol of glycoses;

wherein the sodium hypophosphite is added in an amount of 0.01 mol to 0.1 mol per mol of glycoses; and wherein the so-produced carbohydrate partial esters have an average degree of esterification of 1 to 4.

3. The process of claim 2, wherein:
the potassium carbonate is mixed in an amount of 0.1 mol to 0.15 mol per mol of glycoses;
the glycose comprises sucrose; and
the carbohydrate partial ester comprises a sucrose partial ester esterified with $C_{16}$ and/or $C_{18}$ fatty acids.

4. The process according to claim 2, wherein the average degree of esterification is 3 to 4.

5. The process according to claim 2, wherein step (a), step (b) and step (c) are carried out in an inert gas atmosphere.

6. The process of claim 2, wherein the potassium carbonate and the $C_{16}/C_{18}$ fatty acid methyl esters are mixed at 50 to 100° C.

7. The process of claim 2, wherein the carbohydrate partial ester is a sucrose partial ester.

8. The process of claim 7, wherein the sucrose partial ester is sucrose esterified with $C_{16}$ and/or $C_{18}$ fatty acids.

9. The process of claim 7, wherein the glycose is sucrose.

10. The process of claim 2, wherein water is removed in step (b) at 70-85° C. under a pressure of 1-25 mbar.

11. The process according to claim 2, wherein said carbohydrate partial esters are used for the production of food, cosmetic or superabsorbing end products and said emulsifiers comprise partial esters of carbohydrates, wherein the carbohydrate unit is identical to that of the end product in which the carbohydrate partial esters are to be used.

12. The process according to claim 2, wherein the product from step (c) is further dissolved in an emollient suitable for cosmetic applications or for food applications and, after removal of the unreacted glycoses, is bleached with hydrogen peroxide, under nitrogen, to produce a bleached product.

13. The process according to claim 12, wherein said emollient comprises a hydrocarbon.

14. The process according to claim 13, wherein said hydrocarbon comprises a polyisobutene, liquid at 20° C.

15. The process according to claim 12, wherein a $C_{16}$-$C_{40}$ fatty alcohol or a mixture of $C_{16}$-$C_{40}$ fatty alcohols is added to the product from step (c) to produce a product, which is pelleted, extruded, granulated, crystallized, spray-dried or tabletted.

16. The process according to claim 15, wherein said fatty alcohol comprises a $C_{18}$-$C_{30}$ fatty alcohol or a mixture of such fatty alcohols.

17. The process according to claim 16, wherein said fatty alcohol comprises a $C_{20}$-$C_{24}$ fatty alcohol or a mixture of such fatty alcohols.

18. The process according to claim 15, wherein following addition of one or more fatty alcohols, the product is bleached with hydrogen peroxide.

\* \* \* \* \*